United States Patent [19]
Sato et al.

[11] Patent Number: 5,537,036
[45] Date of Patent: Jul. 16, 1996

[54] HIGH-FREQUENCY MAGNETIC PROPERTY MEASURING APPARATUS WITH WOUND PLANE-SHAPED CONDUCTORS FOR MEASURING SOFT MAGNETIC FILMS

[75] Inventors: Toshiro Sato; Tetsuhiko Mizoguchi, both of Kanagawa-ken, Japan

[73] Assignee: Kabushiki Kaisha Toshiba, Kawasaki, Japan

[21] Appl. No.: 117,840

[22] Filed: Sep. 8, 1993

[30] Foreign Application Priority Data

Sep. 10, 1992 [JP] Japan .................................... 4-242289

[51] Int. Cl.$^6$ .................................................. G01N 27/72
[52] U.S. Cl. ........................ 324/239; 324/260; 324/218; 336/225; 336/178
[58] Field of Search ...................................... 324/228, 239, 324/241, 243, 244, 260, 262, 654, 717; 336/175, 178, 221, 222, 225, 226, 228, 212

[56] References Cited

U.S. PATENT DOCUMENTS 2,477,057  7/1949  Grady, Jr. ............................ 324/239 X
4,243,939  1/1981  Grossman et al. ................... 324/239 X
4,902,997  2/1990  Moran ................................. 324/239 X

OTHER PUBLICATIONS

Calcagno et al., "Semiautomatic Permeance Tester for Thick Magnetic Films", Rev. Sci. Instrum., vol. 46, No. 7, Jul. 1975, pp. 904–908.

Fessant et al., "Influence of In–Plane Anisotropy and Eddy Currents on the Frequency Spectra of the Complex Permeability of Amorphous CoZr Thin Films", IEEE Transactions on Magnetics, vol. 29, No. 1, Jan. 1993, pp. 82–87.

Primary Examiner—Sandra L. O'Shea
Assistant Examiner—Jay M. Patidar
Attorney, Agent, or Firm—Foley & Lardner

[57] ABSTRACT

A high frequency magnetic property measuring apparatus for soft magnetic film includes a magnetic detection device for detecting the intensity of magnetization in a sample material, a high frequency magnetic field generator for generating magnetic field, a power source for supplying current to the magnetic field generator, and a data processing device for getting high frequency magnetic parameters of the sample by using a detection signal output from the magnetic detector. The magnetic field generator is made up of a plane-shaped coil of a conductor having a configuration in which both ends of the plane-shaped coil are closed to form a cavity as a second internal cavity in which the detector is placed. The magnetic detector is made up of a plane-shaped coil of a conductor having a configuration in which both ends of said plane-shaped coil are closed to form a cavity as a first internal cavity in which the sample material is placed. The magnetic detector is placed in the magnetic field generator.

10 Claims, 15 Drawing Sheets

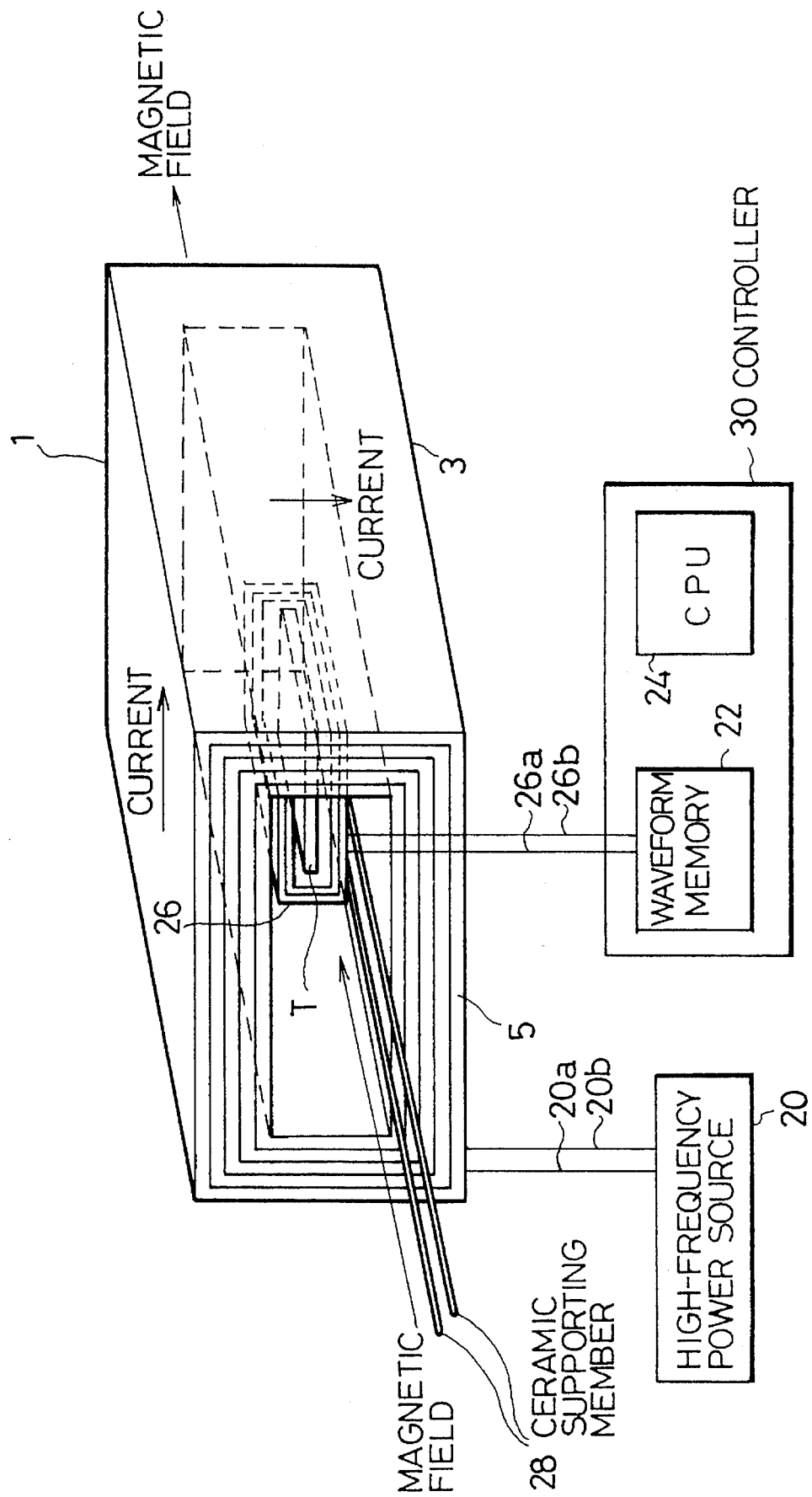

& 1

HIGH-FREQUENCY MAGNETIC PROPERTY MEASURING APPARATUS WITH WOUND PLANE-SHAPED CONDUCTORS FOR MEASURING SOFT MAGNETIC FILMS

TECHNICAL FIELD

The present invention relates to a magnetic property measuring apparatus for measuring magnetic properties of magnetic materials applied to magnetic elements such as a magnetic recording head, inductor, and transformer.

BACKGROUND ART

Recently, the information recording density in magnetic recording systems such as a Video Tape Recorder (VTR) and a Hard Disk Drive (HDD), and the like has greatly increased.

In these high density magnetic recordings information or data is recorded into a recording material by using a short-wave frequency recording, so it is required for the recording media to have a large coercive force. In addition, it is also required for a recording head to use a soft magnetic material having a high saturation magnetic flux density and it is also required for the recording head to have a good frequency property corresponding to the increase in recording frequency. In particular, it is required that the magnetic head be applied to a HD-VTR (High Definition Video Tape Recorder) and a high density HDD head operate for frequencies of up to several ten MHz.

On the other hand, in miniaturization of various electronic devices, it is also required to miniaturize power source section in the electronic devices. In order to answer the above requirements, a switching power supply in which switching frequency is increased is used in electronic devices. Although the switching power supply has been miniaturized by using miniaturized magnetic components such as a high frequency inductor or a high frequency transformer, however it is difficult to miniaturize the magnetic components.

In order to overcome the problem described above, a thin film magnetic element using a soft magnetic thin film is currently under investigation. Since this thin film magnetic element can operate for frequencies of a few MHz to several ten Mhz, it would be used for the switching power supply.

In addition, the soft magnetic material is used for the high frequency magnetic elements described above, soft magnetic materials of alloy system, oxide system, nitride system, and the like have been developed.

As shown in FIG. 1, a high frequency core loss measuring device which operates in a range up to 20 Mhz has been developed as a magnetic property measuring means for a bulk magnetic material. This high frequency core loss measuring system is actually used as an evaluation equipment for research of material development. A feature of the measuring method for measuring the property of the bulk magnetic material is that the intrinsic property of material can be measured without demagnetization effect by using a ring-shaped soft magnetic material sample T.

However, there are many problems when the measuring method of the conventional magnetic property measuring system shown in FIG. 1 is directly utilized for a thin film sample. In FIG. 1, the sine wave signal generator 101 provides a frequency signal. The power amplifier 103 provides current to the sample T via lines 105a, b. A wave-form storage device 109 stores the waveform provided through signal transfer lines 107a, b. A computer 111 controls the sine wave signal generator 101, the power amplifier 103 and the wave-form storage device 109. For example, in one of the problems, although a measuring frequency is usually limited by a self-resonance frequency, it is difficult to increase a self-resonance frequency because a coil is directly wound in a soft magnetic thin film as a sample in the measuring method shown in FIG. 1. Further, a thin film is usually formed on a substrate and the thin film to be measured must be wound together with a coil, so that a large measuring error is caused in results measured for the thin film by the existence of the substrate. In order to eliminate the measuring error, Calcagno et al. have proposed a magnetic thin film measuring method using an 8-figure coil. (see the reference of Rev. Sci. Instrum., Vol. 46, No. 7, pp. 904–908, 1975)

FIGS. 2A and 2B show the principle of the magnetic thin film measuring method. In the magnetic thin film measuring method using the 8-figure coil, first, a thin film 123 as a sample of a soft magnetic material is formed on a substrate 125. Then, the thin film formed is located in a uniform high frequency magnetic field and placed in the upper coil (or the lower coil) of the 8-figure coil 121a in order to measure the properties of the thin film.

The magnetic thin film measuring method will now be described below abstractly. Here, we assume that a sample of a soft magnetic material or a body to be measured is placed in the upper coil just as the thin film penetrates the upper coil. The magnetic flux $\phi_o$ passing through the upper coil is:

$$\phi_0 = S_b \cdot \mu_0 (H - H_d) + S_a \cdot I \tag{1}$$

where $S_a$ is a sectional area of a soft magnetic material to be measured, $S_b$ is a sectional area of the upper section of the 8-figure coil 121a shown in FIG. 2B, H is an external high frequency magnetic field, is vacuum magnetic permeability, $H_d$ is a demagnetizing field in the inner section of a sample, and I is a magnetization of a sample of a thin film.

The magnetic flux $\phi$ passing through the lower coil in which the soft magnetic material sample is not placed is:

$$\phi_0 = S_b \cdot \mu_0 (H - H_r) \tag{2}$$

where $H_r$ is the demagnetizing field in the entire section of a sample.

A pair of coils of the 8-figure coil are connected to each other in anti-polarity. Therefore the value of an induced voltage becomes following:

$$V_g = -(d\phi_0/dt - d\phi/dt) = -S_0 \cdot (dI/dt) + S_a \cdot (d(H_d - H_r)/dt) \tag{3},$$

where H is an external high frequency magnetic field,

Here, when the Hr is approximately equivalent to the $H_d$, the magnetization I of the sample thin film is given as follows:

$$I = (1/S_a) \int V_g \cdot dt \tag{4}.$$

In addition, in a measuring process, a magnetic field detecting coil 121b is placed adjacent to the sample to detect the external high frequency magnetic field. In this case, the value of $H_{eff}$ is given as follows:

$$H_{eff} = (1/S_c) V_H \cdot dt \tag{5}$$

where $S_c$ is a sectional area of a magnetic field detecting coil 121b, shown in FIG. 2B.

Thus, we can know the values of the external magnetic field H and of the magnetization I of the sample of the thin film, when the rate of amplitudes of these values is obtained, the high frequency effective magnetic susceptibility $X_{Eff}$ is obtained as follows:

$$X_{Eff} = I_m/H_{Eff.\ m} \quad (6)$$

where $I_m$ and $H_{Eff.\ m}$ are the peak values.

In addition, the value of the high frequency effective magnetic permeability $\mu_{Eff}$ is following:

$$\mu_{Eff} = X_{Eff} + 1 \quad (7).$$

As described above in detail, the 8-figure measuring method is widely used as a measuring method for a high frequency magnetic permeability because it has good availability. However, the applications of the measuring method are limited only within small signal measurement, for example, magnetic field amplitude of approximately 0.5 A/m.

Further, as shown in FIG. 3, a conductor is only wound in 8-figure form as a 8-figure coil. In this case, the dimension of a looped-area of the upper coil of the 8-figure coil must be equal to that of the lower coil exactly in order to obtain a correct measured value.

However, usually, it is very difficult to form the upper section and the lower section of the 8-figure coil whose looped-areas are equal to each other by using the winding method for winding with a conductor. The dimension error of the looped-areas between the upper section and the lower section of the 8-figure coil effects the measuring accuracy directly.

In order to avoid the conventional problem described above, as shown in FIG. 4, a method for forming a 8-figure coil is proposed by using printed circuit board technology. With the 8-figure coil obtained by the forming method, the dimension accuracy can be easily increased. In an actual measuring process, the dimension error of the 8-figure coil is modified by a calibration based on a detected voltage when a sample to be measured is not inserted in the 8-figure coil.

Further, a sample thin-film is placed in the 8-figure coil as shown in FIG. 2A, in this case, the magnetization change of the entire sample thin-film cannot be detected because a magnetization change of an area positioned only nearby the 8-figure coil is measured. For example, as shown in FIG. 5, when there are triangle magnetic domains in the edge sections of the sample thin-film, the property of a magnetic component with the magnetic thin-film is affected by the existence of the triangle magnetic domains, and the conventional method using the 8-figure coil can detect only a local magnetization change in a sample.

There is the difference between the magnetic property of a sample thin-film itself to be measured and the electrical property of magnetic elements including the triangle magnetic domains generated in the sample thin-film. Specifically, the conventional measuring method cannot detect the magnetization change of the overall property of a soft magnetic material as a sample.

In addition, as shown in FIG. 6, a parallel plane-shaped coil is also often used as a means for generating a high frequency uniform external magnetic field. However, according to the study by the inventors of the present invention, it is apparent that the parallel plane-shaped coil can't generate a homogenous magnetic field. FIGS. 7A to 7C show calculation results about a magnetic field distribution in the parallel plane-shaped coil by using Biot-Savart law.

As shown in FIGS. 7A to 7C, there is a fluctuation of the magnetic field of more than 20 percent in the range of the center point 0±7 mm in the parallel plane-shaped coil.

The fluctuation of the magnetic field, namely irregular magnetic field, affects the measuring accuracy of a sample.

As described above in detail, it is required to perform high frequency magnetic measurements with a large signal operation. For these reasons or requirements, the magnetic property evaluation of these high frequency magnetic elements must be performed in a high frequency magnetic field having a large amplitude which is almost equivalent to an actual amplitude of a high frequency magnetic field in which a soft magnetic material is actually used in application fields.

Moreover, it is required to obtain a method or a technique for evaluating magnetic components affected from the magnetic property of the entire soft magnetic material. However, at present, there is no method for evaluating the effects, so that development of a magnetic recording head, a thin film inductor, a thin film transformer, and the like is limited.

SUMMARY OF THE INVENTION

Accordingly, an object of the present invention is to provide an improved high frequency property measuring apparatus to evaluate soft magnetic materials.

Another object of the present invention is to provide a magnetic property measuring apparatus which can evaluate the overall properties of magnetic material in a wide range of a magnetic amplitude when the magnetic material is measured, which is applied to a magnetic recording head, a thin film inductor, a thin film transformer, and the like.

According to one aspect of the present invention, there is provided a magnetic property measuring apparatus having: detection means for detecting the intensity of magnetization generated in a material to be measured, comprising a plane-shaped coil formed by a plane-shaped conductor whose pair of end faces are closed and has an internal cavity as a first cavity, in which said measuring material is placed; magnetic field generation means for generating a magnetic field, comprising a plane-shaped coil formed by a plane-shaped conductor whose pair of end faces are closed and has an internal cavity as a second cavity, in which said detection means is placed; a high frequency power source for supplying current to said magnetic field generation means; and detection control means for a high frequency property of said material by using a detection signal output from said detection means.

According to another aspect of the present invention, there is provided a magnetic field generation device for generating a magnetic field comprising: a plane-shaped coil consisting of a plane shaped conductor whose end faces are closed and which has an internal cavity, wherein said magnetic field generation device generates a magnetic field based on a current provided from an external device.

Further, according to another aspect of the present invention, there is a provided a magnetic property measuring device for detecting the intensity of magnetization generated in a material to be measured, comprising: a plane-shaped coil consisting of a plane shaped conductor whose pair of end faces are closed and which has an internal cavity, wherein said magnetic property measuring device detects the intensity of magnetization generated in said material placed in said internal cavity of said plane-shaped coil.

BRIEF DESCRIPTION OF THE DRAWINGS

These and other objects, features, and advantages of the present invention will become more apparent from the following description of the preferred embodiments taken in conjunction with the accompanying drawings, in which:

FIG. 8 is a perspective drawing showing a schematic configuration of a high frequency magnetic property measuring apparatus for a soft magnetic material as an embodiment according to the present invention.

DETAILED DESCRIPTION OF THE PREFERRED EMBODIMENTS

Figure 1:
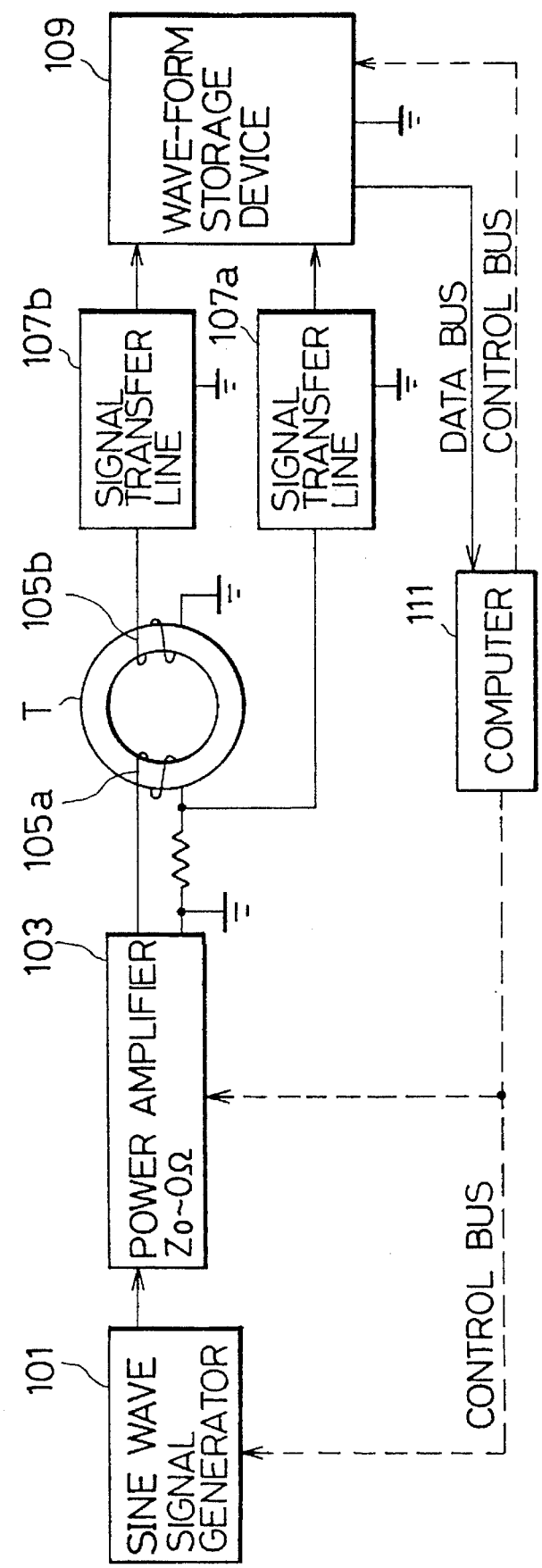
FIG. 1 is a block diagram showing a schematic configuration of a conventional high frequency magnetic property (a core loss) measuring apparatus for a soft magnetic material.
Figure 2A:
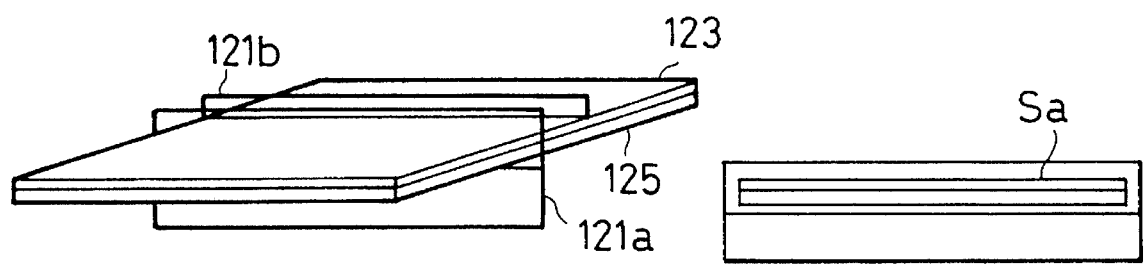
FIGS. 2A and 2B are diagrams showing an magnetic thin film measuring method by using a 8-figure coil.
Figure 2B:
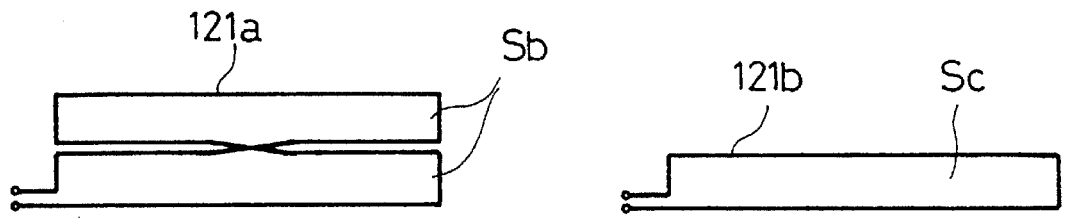

Other features of this invention will become apparent in the course of the following description of exemplary embodiments which are given for illustration of the invention and are not intended to be limiting thereof.

A preferred embodiment of a magnetic property measuring apparatus according to the present invention will now be described below.

First, with referring to FIGS. 8 to 12 we will explain a magnetic field generating device 1 which is shown in a perspective drawing of the magnetic property measuring apparatus for a soft magnetic material shown in FIG. 8. The magnetic field generating device 1 receives a high frequency current provided from a power source 20, then generates a homogeneous high frequency magnetic field used for measuring the high frequency magnetic properties soft including a high frequency magnetic permeability and a high frequency power loss of a soft magnetic material. One example of a configuration of the magnetic field generating device 1 is shown in FIG. 8 in which appropriate plane-shaped conductor conductors 3 are wound repeatedly. Each layer is insulated with an insulating layer 5 which is made up of a low dielectric constant or a relative permittivity material. The air is the best insulating layer ideally, but a material which has a relative dielectric constant, whose value is near to 1, is acceptable for the insulating layer. For example, in a fabrication process of the magnetic field generating device, a conductor is bonded with an appropriate insulating substrate such as glass, polyimide, and the like, then it is wound repeatedly just as it's cross section takes a rectangular form.

As shown in FIG. 8, in the magnetic field generating device 1, a magnetic detecting device 26 is placed as a detection means. The magnetic detection device 26 is supported in a magnetic field generating device 1 by a ceramic supporting member 28 made of ceramic and placed at a center portion of a cave.

In addition, a soft magnetic material T which is an object sample to be measured is placed in the magnetic field detection device 26.

Data relating to the signal of the object measuring material T and the signal in which there is no object sample to be measured is transferred to a wave form memory 22 in a control device 30, then arithmetic operation is performed by a CPU 24 in order to calculate the value of the magnetization of the object sample. As shown in FIG. 8, it is desirable that the signal lines 26a and 26b between the magnetic detection device 26 and the wave form memory 22 are adequately separated from each other to prevent an electrical short.

Figure 13:
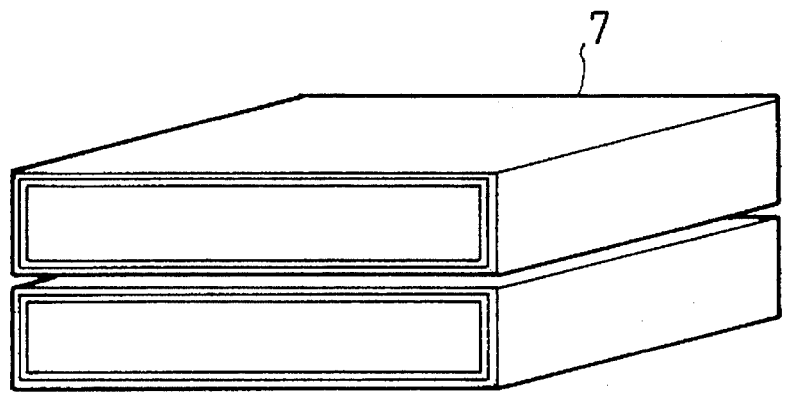
FIG. 13 is a perspective diagram of a configuration of an 8-figure plane coil.
Figure 14A:
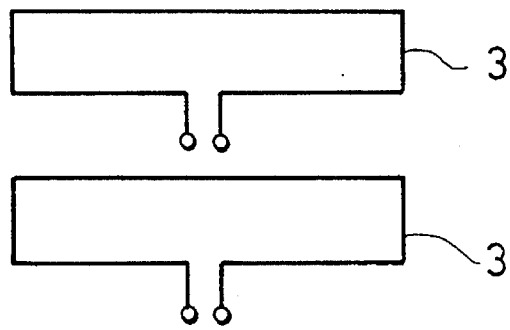
FIGS. 14A and 14B are schematic diagrams of the 8-figure shaped plane coil when it detects a voltage value with the upper and lower coils thereof.
Figure 14B:
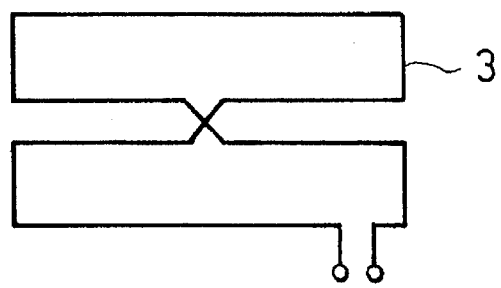

In addition, the magnetic detection device 26, as described below in detail, consists of one plane-shaped coil. But, the scope of the present invention is not limited to this configuration. For example, it is possible to make a magnetic detection device 7 having two plane-shaped coils, as shown in FIGS. 13 and 14A, 14B.

Figure 9A:
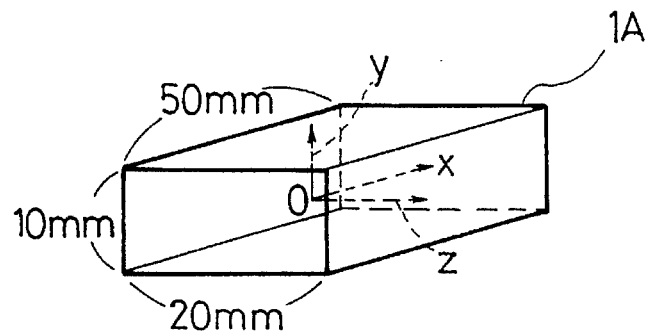
FIGS. 9A to 9C are diagrams showing the feature of a homogeneous magnetic field generated by the high frequency magnetic generating means shown in FIG. 8.

FIG. 9A is a configuration of a magnetic field generating device 1A having a rectangular-shaped form of 10 mm×20 mm which is made by winding one time a plane-shaped conductor 3 of 50 mm wide.

Figure 9B:
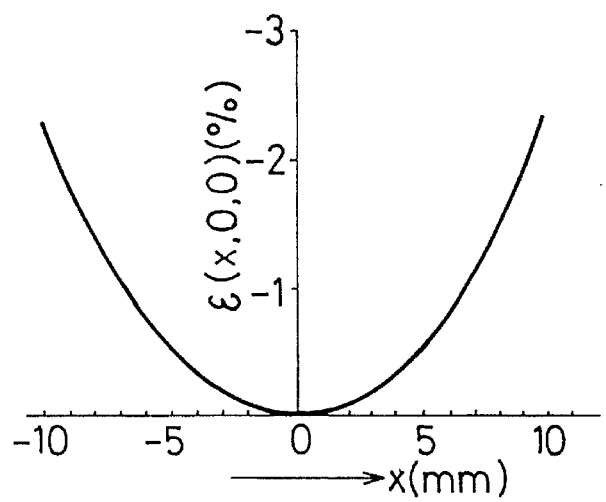
Figure 9C:
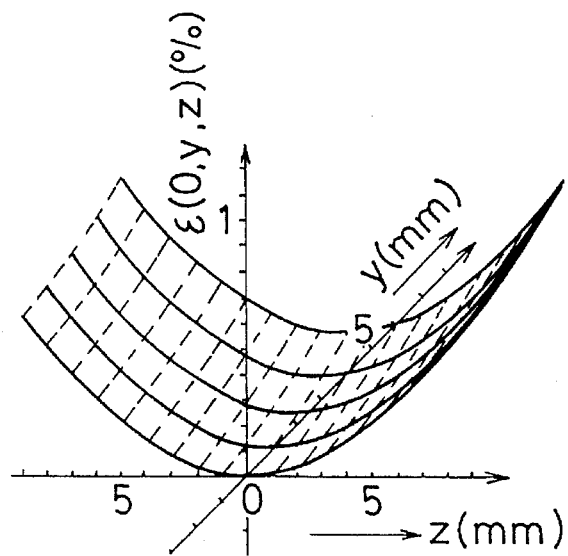

FIGS. 9B to 9C show the results of homogeneous magnetic field generated by the magnetic field generating device 1A. Here, s is given by the following definition:

$$\epsilon = (H(0,0,0) - H(x,y,z))/H(0,0,0) \times 100\% \tag{8}$$

where, H(0,0,0) is the magnitude of a magnetic field at a central point O of a rectangular-plane-shaped coil, and H(x,y,z) is the magnitude of a magnetic field of an optional point in the rectangular-plane-shaped coil.

As shown in FIGS. 9A to 9C, the homogeneous magnetic field is kept within a 1% error in the range of (x,y,z)=(±7 mm,±7 mm,±10 mm) on the basis of the point (0,0,0).

Figure 3:
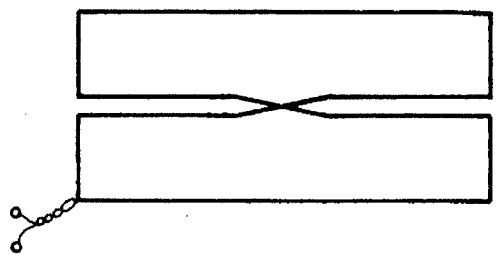
FIG. 3 is a configuration diagram of a conventional 8-figure coil.
Figure 4:
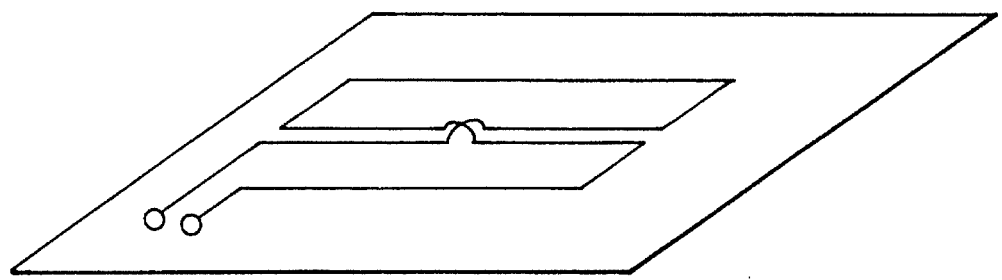
FIG. 4 is an another configuration diagram of a conventional 8-figure coil.
Figure 5:
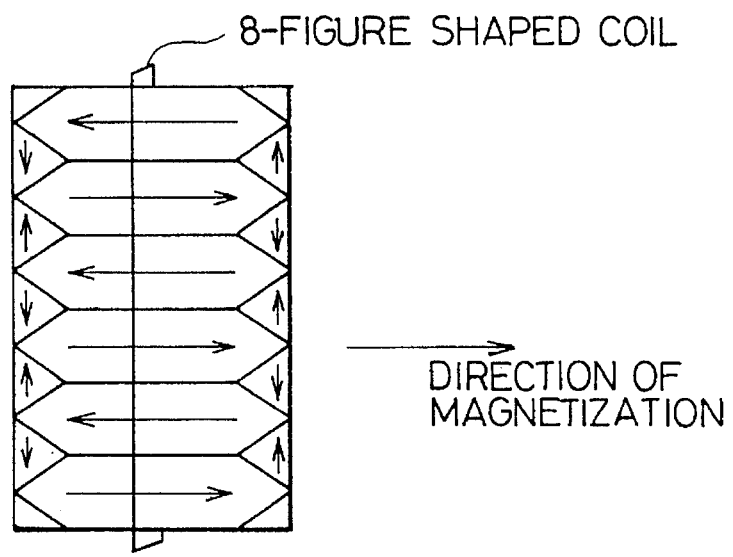
FIG. 5 is a diagram showing an example of a pattern of magnetic domains of an object sample to be measured.
Figure 6:
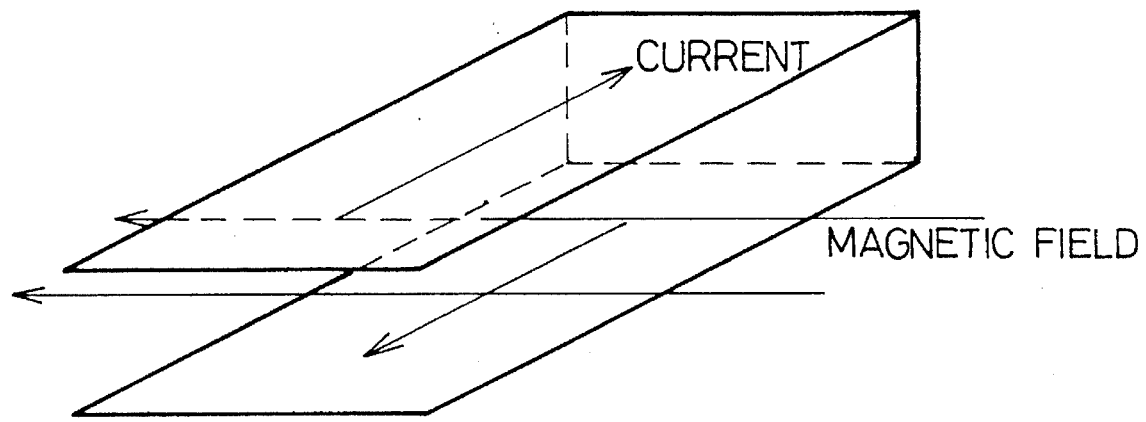
FIG. 6 is a perspective diagram showing a schematic configuration of a conventional high frequency magnetic field generating means.
Figure 7A:
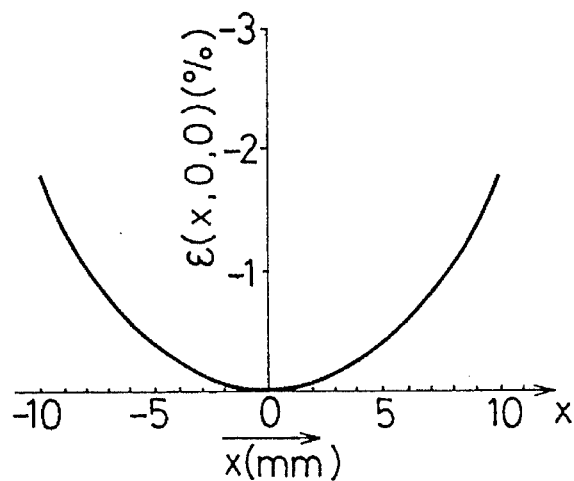
FIGS. 7A to 7C are graphs showing the property of a magnetic field distribution obtained by a conventional high frequency magnetic generating means based on the Biot-Savart law.
Figure 7B:
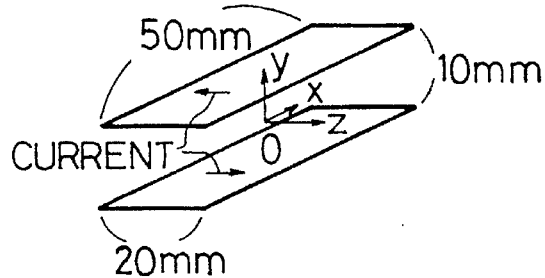
Figure 7C:
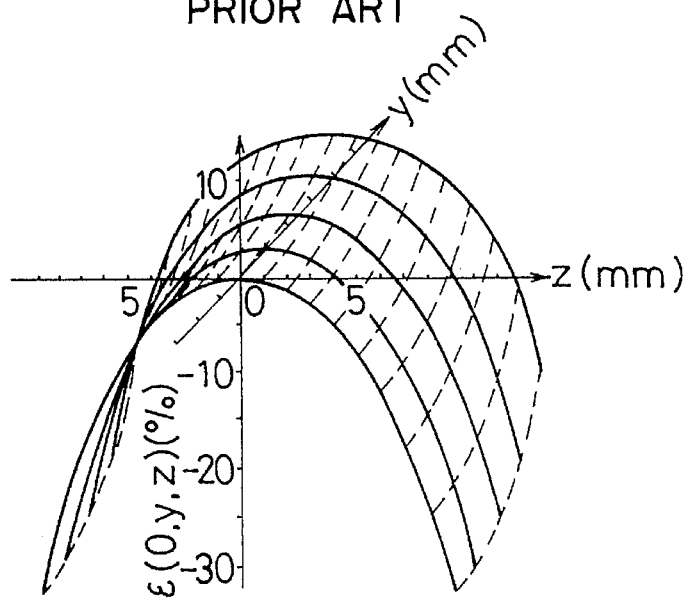

Comparing with the conventional parallel plane coil shown in FIG. 3, this rectangular-plane-shaped coil can generate a good homogeneous magnetic field. In the magnetic generating device 1, when a large area of the homogeneous magnetic field is needed, it can be obtained by use of a rectangular multi plane shaped coil having a longer width. It can be modified by adjusting to a size of a soft magnetic material which is a measuring object. In other words, when the size of a sample is approximately 10 mm, the homogeneous magnetic field of a range of ±5 mm from the central point of the coil must be kept. In an actual fabrication process, there is no problem when the homogeneous magnetic field is generated in a range of approximately 1.5 times of a sample size.

Figure 10:
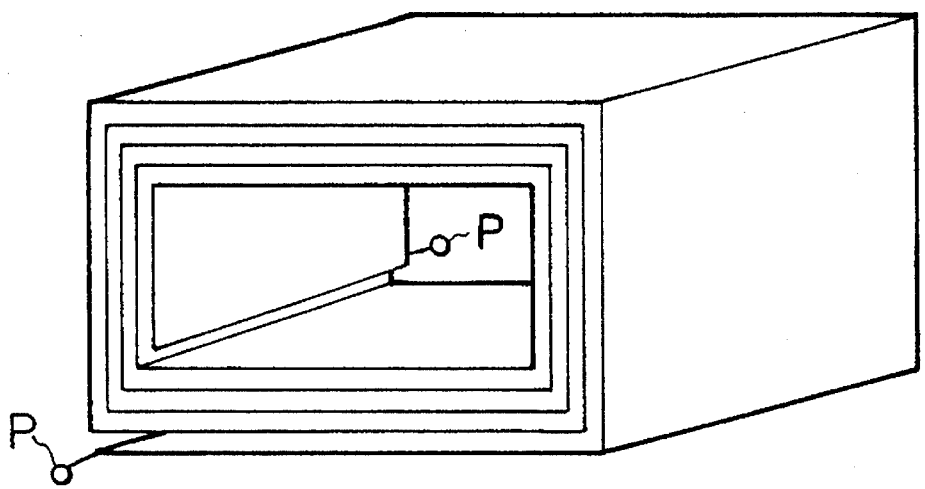
FIG. 10 is a perspective diagram showing a configuration of a rectangular multi-plane-shaped coil as the high frequency magnetic generating means shown in FIG. 8.

In order to increase the magnitude of a magnetic field of a section nearby the central point of a coil, a rectangular plane-shaped coil is wound a number of times like the magnetic field generating device 1. In this case, when rectangular plane-shaped coils of multi layers are connected in series, as shown in FIG. 10, the amplitude of the magnetic field which can be generated per current is increased, but the impedance of the coil becomes large.

Figure 11:
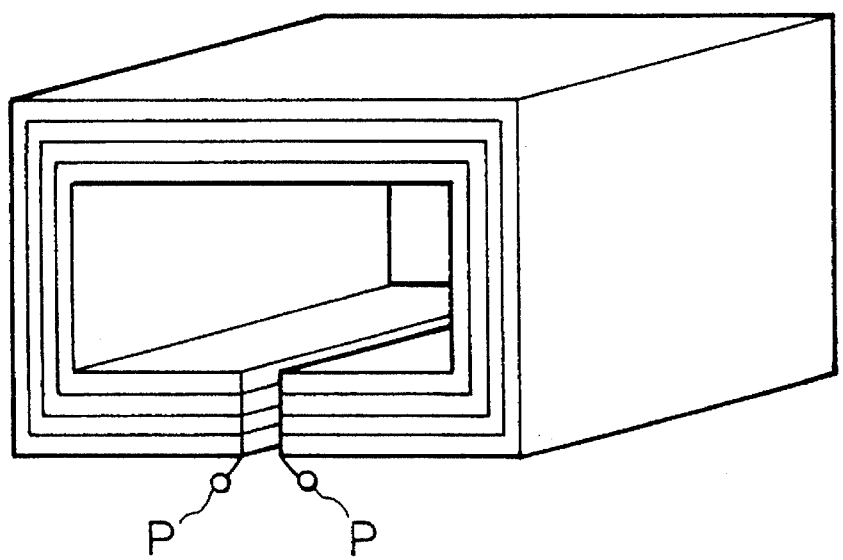
FIG. 11 is a perspective diagram showing another configuration of a rectangular multi-plane-shaped coil as the high frequency magnetic generating means shown in FIG. 8.

On the other hand, as shown in FIG. 11, when rectangular plane shaped coils are connected in parallel, the amplitude of the magnetic field per current becomes small in addition to decreasing the impedance of the entire coils.

Figure 17:
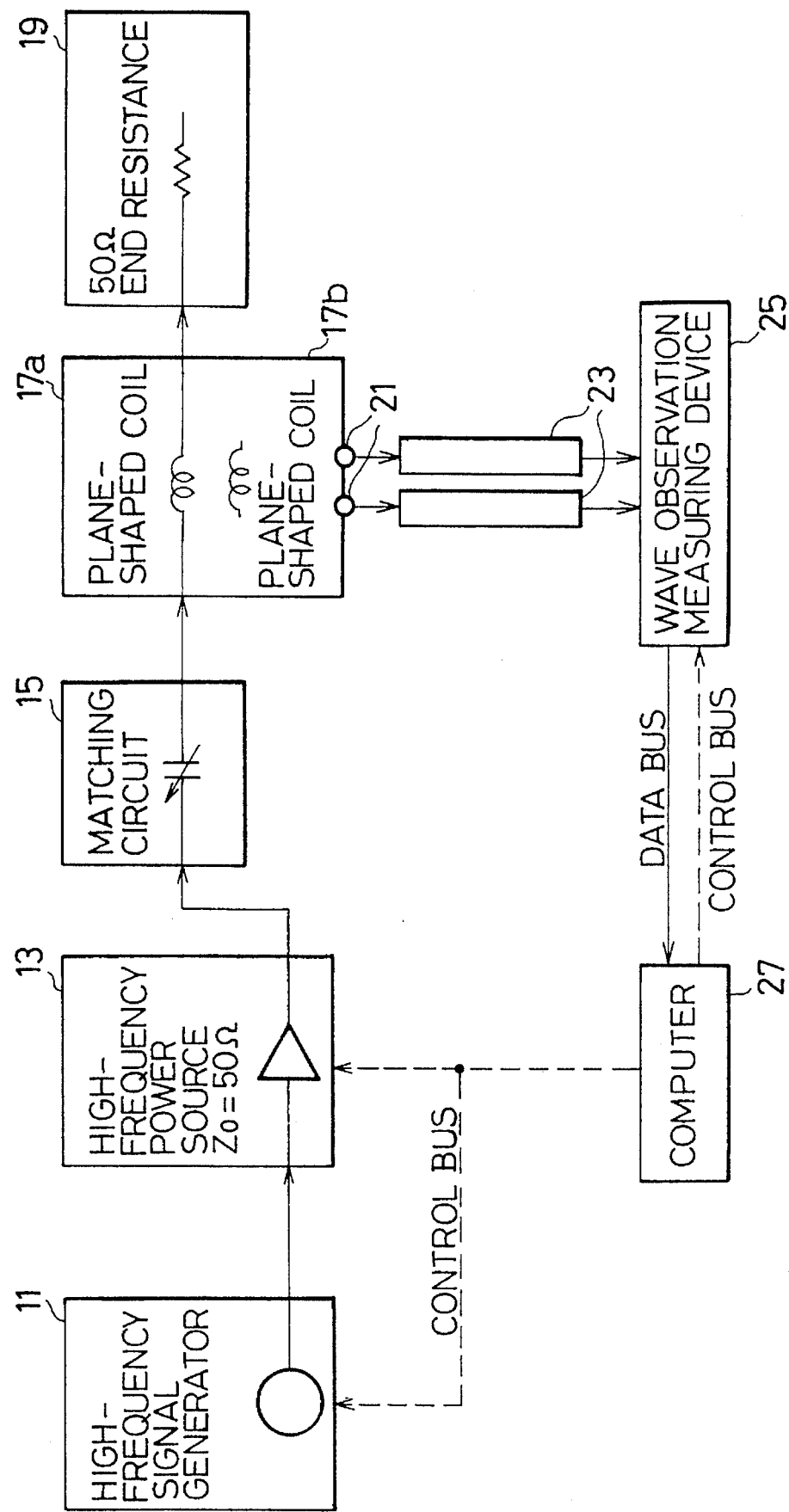
FIG. 17 is a block diagram showing a schematic organization of a high frequency magnetic property measuring apparatus for a soft magnetic material.

In both cases shown in FIGS. 10 and 11, there is no problem with the impedance even if one of the coils described above is used because a matching circuit 15, which is described below in detail as shown in FIG. 17, is placed with a power source 13 generating a high frequency current and rectangular multi-wound-plane-shaped coil 17a consisting of a magnetic field generating means. For example, when the amplitude of output current is sufficiently large it is better that each layer of the rectangular multi-wound-plane-shaped coils is connected in parallel. In reverse, it is better that each layer of the rectangular multi-wound-plane-shaped coils 17a is connected in series. In addition, as shown in FIG. 8, it is desirable that the pair of lines 20a and 20b between the magnetic field generating device 1 and the high frequency power source are adequately separated from each other to prevent an electrical short.

Figure 12A:
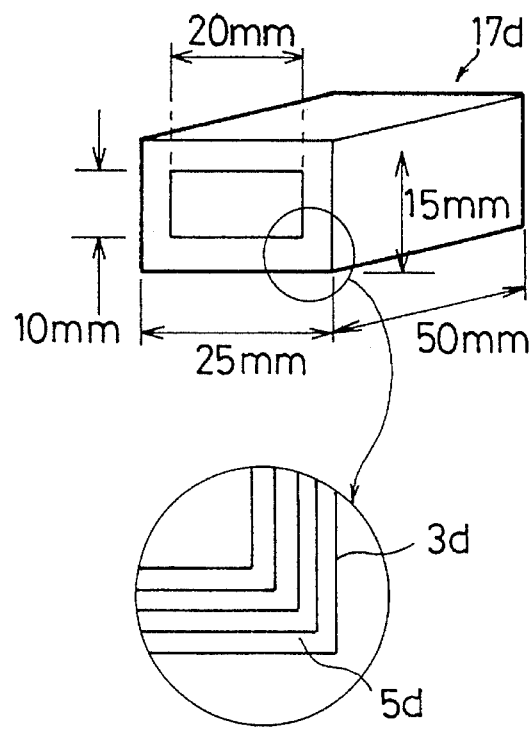
FIG. 12A is a configuration diagram of a rectangular multi-plane-shaped coil.
Figure 12B:
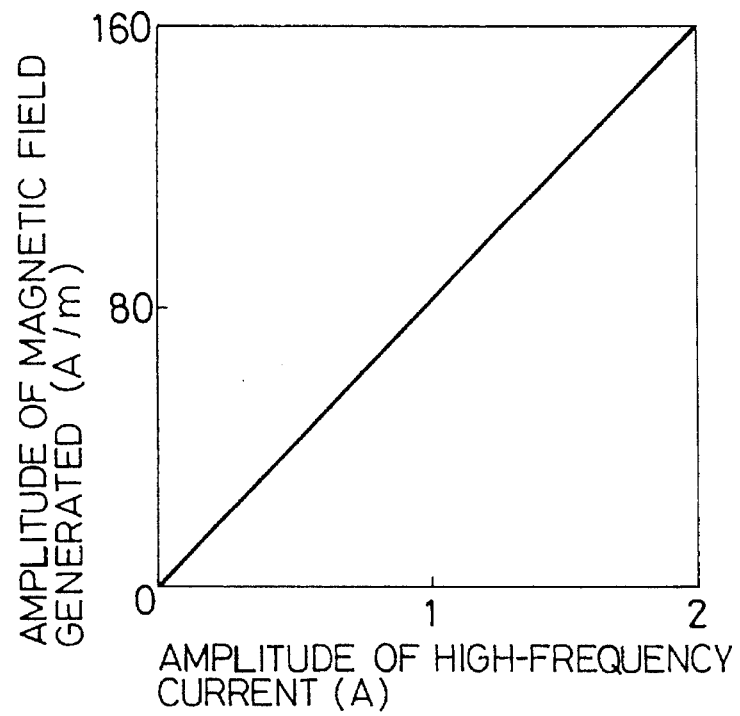
FIG. 12B is a diagram showing a relationship between the amplitude of a high frequency current of 50 MHz and the amplitude of a magnetic field generated.

Next, with reference to FIGS. 12A and 12B, a property of rectangular multi-wound-plane-shaped coils 17d, shown in FIG. 12A, whose cross section is the area of 15 mm×25 mm will be explained below.

First, 0.2 mm thick copper is plated on a glass substrate of 1 mm thick in order to form a layer by using an electroless plating method after Cr is evaporated on the substrate with several hundred angstroms, for example with 500 angstroms, then cut off the glass substrate with a predetermined dimension in order to obtain a rectangular multi-wound-plane-shaped coil 17d which is wound 5 times and includes conductor 3d and insulators. The copper in each layer is bonded with a copper paste.

Further, a high frequency current of 50 MHz flows in the rectangular multi-wound-plane-shaped coil 17d. FIG. 12B is a graph showing measured results of a magnetic field generated in the coil by using a searching coil of 1 mm in diameter used for measuring the amplitude of the magnetic field in the core. From the results, the amplitude of the high frequency magnetic field reaches 80 A/m per current amplitude of 1 A, the distribution of the magnetic field in the coil has a homogeneous distribution by using the same measuring method described above in which the distribution at a point of ±5 mm from the central point of the coil becomes within 1%, the distribution at a point of 10 mm from the central point of the coil becomes within 2%.

By using the magnetic field generating means consisting of the rectangular multi-wound-plane-shaped coil 17d described above, a soft magnetic material can be easily placed for measuring it in a homogeneous high frequency large amplitude magnetic field.

In the present invention, a cross section of a magnetic field generating means is not limited to the configuration having a rectangular-shaped form described above in the embodiment, for example it can have the same effects when a cross section of the magnetic field generating means is a circle shape or an ellipse shape. However, a rectangular shape or a square shape is required in order to generate a homogeneous magnetic field.

Next, with referring to FIGS. 13 and 14A to 14B, the magnetic field device 7 will be explained below.

FIG. 13 is a perspective diagram of the magnetic detection device 7 in which a 8-figure coil to detect a magnetic field of a soft magnetic material as a measuring sample consists of a plane-shaped conductor.

Although the dimension of the 8-figure coil is determined by the relationship between a sample size and a homogeneous magnetic field in a magnetic field generating coil, it requires more than the size of a sample in order to detect exactly and correctly information of the magnetization of the entire sample.

Actually, there are two types of 8-figure shaped coils. In the first method, as shown in FIG. 14A, the upper section of the 8-figure coil is not connected to the lower section of it so that a detected signal is output independently from each section. In this method, the calculation of the equation (3) prescribed is performed.

In the second method, as shown in FIG. 14B, the upper coil of the 8-figure shaped coil is connected with the lower coil of the 8-figure shaped coil in anti-polarity so that the detected voltage is obtained by the equation (3).

Next, in the first method, it can eliminate an adverse effect caused by when the looped area in the upper coil is completely different from the looped area of the lower coil by an appropriate arithmetic calculation. Specifically, although a voltage wave-form detected from the upper rectangular plane-shaped coil when a soft magnetic material sample is not placed in it must be completely equivalent to that of the lower rectangular plane-shaped coil, when the both voltage wave forms are different, the difference between both coils in area size can be almost completely corrected by using the amplitude rate of both voltages detected as a correction factor.

We will further explain the correction method in detail below. When the looped areas of the upper- and lower-rectangular plane-shaped coils are S1 and S2, respectively, and the high frequency magnetic field is H, the induced voltage $V_1$ and $V_2$ become as follows:

$$V_1 = S_1 \cdot (d(\mu_0 \cdot H)/dt) \tag{9}$$

$$V_2 = S_2 \cdot (d(\mu_0 \cdot H)/dt) \tag{10}$$

When the areas $S_1$, $S_2$ of the looped coils are different in area and the amplitude rate k of the reduced voltages is a correction factor, $V_1$, and $V_2$, the error caused by the difference in area between the both looped-coils can be eliminated. In this case, the effect of a signal transmission property from the coil to the measuring instrument is included in the voltage wave-form measured by the measuring instrument. Therefore, this effect must be reduced in measurement, or correction is required, in order to reduce the transmission property effect.

In addition, in the method, one coil in which no sample is placed can be also used as an external magnetic field detecting coil for detecting external high frequency magnetic field for a sample of a soft magnetic material because the upper rectangular plane-shaped coil is independent from the lower rectangular plane-shaped coil. Therefore, an external magnetic field detecting coil is not required.

On the other hand, by using the second method described above, it is not easy to execute an appropriate correction process for detected voltages of both coils. That is, the voltage $V_8$ detected when the area of the upper rectangular plane shaped coil is different from that of the lower rectangular plane shaped coil in area is following:

$$V_8 = (S_1 - S_2) \cdot (d(\mu_0 \cdot H)/dt) \tag{11}$$

In the equation (11), although information about the area size for the both coils is included, it is impossible to separate the area information of the coils.

Accordingly, it is better to use the first method when the 8-figure coil is used. Further, any external magnetic field detection coil is not required so long as the first method is used.

Next, with reference to FIGS. 15A to 15D, an actual fabricating method of the 8-figure coil will be explained below.

Figure 15A:
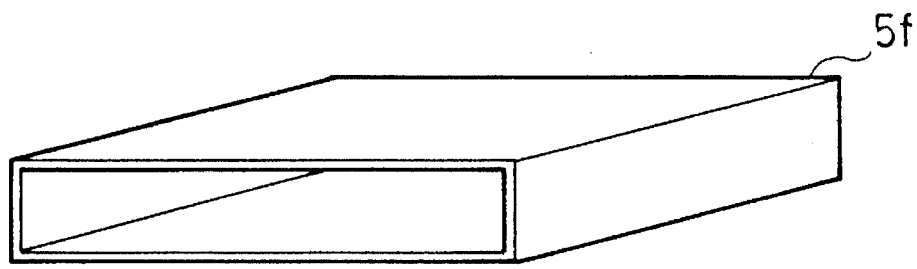
FIGS. 15A to 15D are perspective diagrams showing fabrication procedures for fabricating an 8-figure plane coil.
Figure 15B:
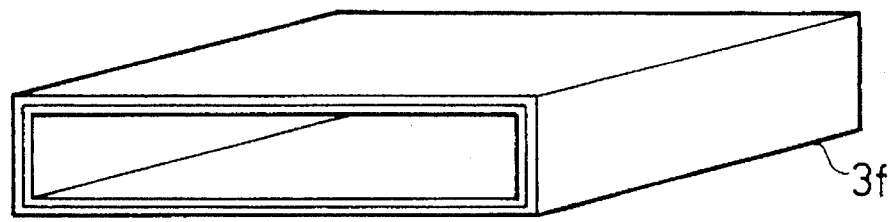
Figure 15C:
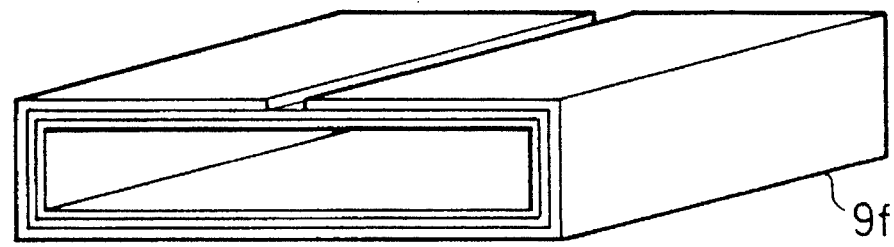

First, as shown in FIGS. 15A and 15B, a copper layer $3f$ on the entire outside surface of a hollow glass box $5f$ of a rectangular shaped is formed by a plating method, a spattering method or a vacuum evaporation method after Cr is evaporated on the substrate.

Next, a photosensitive material is plated on the upper surface of the hollow glass box $5f$. Then, by using a photolithographic method, a patterning step is performed (see FIG. 15C). After the patterning step, the copper layer on the upper surface of the hollow box $5f$ is etched by using the mask pattern obtained by the patterning step, then the photosensitive resin $9f$ is eliminated (see FIG. 15D) in order to obtain a desired copper pattern. Further, by using the same fabrication method described above, another hollow glass box having the same copper pattern is also formed. These two hollow glass boxes are connected like the wiring pattern shown in FIG. 14A.

Figure 16:
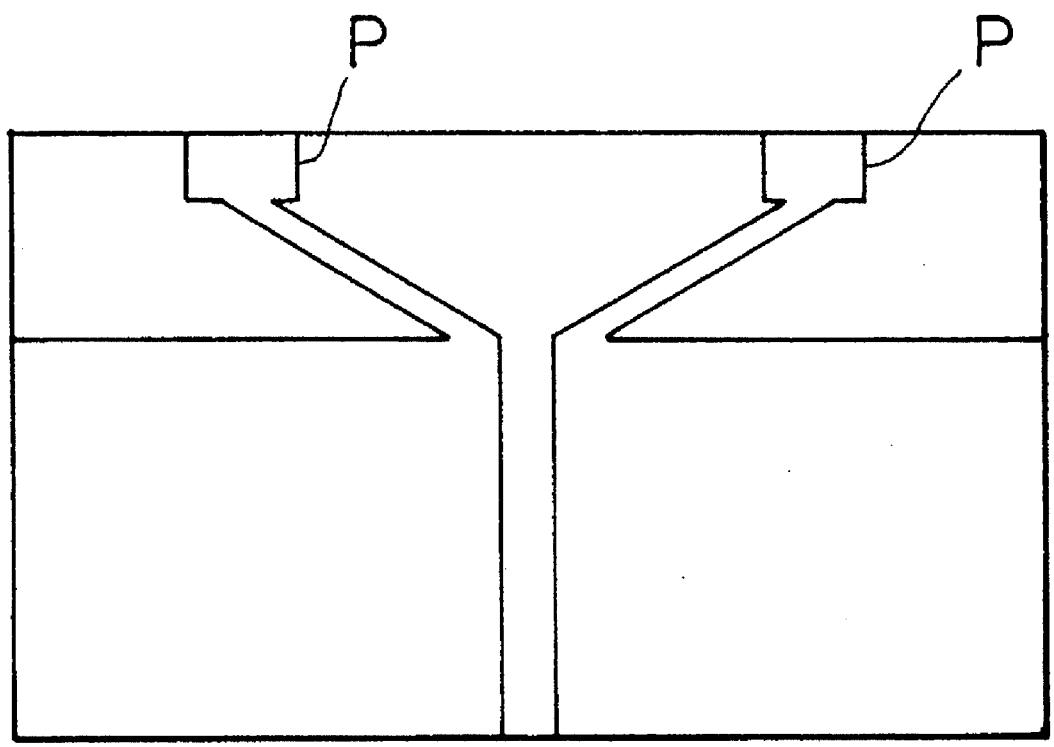
FIG. 16 is a diagram showing an example of a terminal of an 8-figure plane coil.

In addition, a terminal P is formed at one end section of the 8-figure coil, as shown in FIG. 16, in order to connect to a wave-form measuring device 25 through a signal transfer cable 23. In order to eliminate the influence from the signal transfer cable as low as possible, it is preferable to use a probe having a higher impedance. For example, the use of a FET probe is better.

In spite of the use of the FET probe, when the effect of the signal transfer cable is great, or in order to further reduce the effect of the signal transfer cable, before measuring the induced voltage of the coil, the property of the signal transfer cable is measured. Then, by using the property of the cable, the correction operation is performed.

By using the 8-figure shaped coil formed by the fabrication method described above, the entire magnetic property of the measuring sample can be detected. However, the fabricating method to form the 8-figure shaped coil is not limited by the embodiment above.

Next, a third method for detecting a magnetization and a magnetic field will now be described below.

Figure 15D:
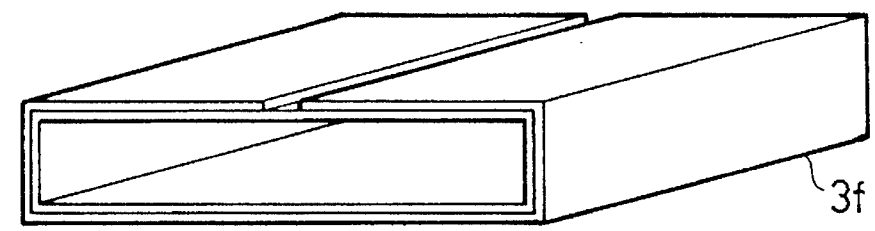

In the third method, a plane shaped detection coil shown in FIG. 15D is used. In this case, the magnetization of a sample and the external magnetic field are detected by one plane shaped detection coil. First, the external magnetic field waveform detected by the plane shaped coil shown in FIG. 15D and is stored along at least more than one period into a waveform memory equipment. Secondly, when a measuring sample is placed within the plane shaped coil, the waveform including an external magnetic field and magnetization of a sample is stored along at least more than one period into the waveform memory equipment. Finally, the change in the difference of the intensity and phase between the measuring sample and the reference data stored in the waveform memory equipment is calculated. By this third method, there is basically no problem about the dimensional difference in areas between the upper coil and the lower coil and about the connection between two coils such as an upper coil and a lower coil.

Therefore by using the third method we can get a high order accuracy measurement.

Next, with reference to a block diagram shown in FIG. 17, a schematic configuration of a magnetic property measuring apparatus using the rectangular multi-wound-shaped coil 17a and the 8-figure-shaped coil 17b prescribed will now be explained.

In the diagram, the high frequency signal generation device 11 generates a high frequency signal. The high frequency power source 13 provides a high frequency current based on the high frequency signal output from the high frequency signal generation device 11 to the rectangular multi-wound-plane-shaped coil 17a. The difference of impedances between the power source and the rectangular multi-wound-plane-shaped coil as a magnetic field generating coil is matched with a matching circuit 15 and an end resistance 19. Specifically, the impedance of the multi-wound-plane-shaped coil 17a is increased when the frequency is increased. In order to compensate the influence of the change, a high frequency variable condenser is connected between the high frequency power source 13 and the rectangular multi-wound-plane shaped coil 17a in series, further, the end resistance 19 having the same value (for example 50 ohm) of output impedance of the high frequency power source 13 is connected in series.

In the configuration of the apparatus shown in FIG. 17, when the high frequency variable condenser is tuned with the multi-wound-plane-shaped coil 17a, this is equivalent to the state that the high frequency power source 13 is connected to the end resistance 19 whose impedance is equal to the output impedance of the high frequency power source.

Accordingly, the high frequency electric power can be provided efficiently from the power source 13.

As described above, the 8-figure coil 17b is formed by two plane-shaped coils configured in parallel like an 8-figure form, the cross section of the 8-figure coil becomes a rectangular shape, and the two plane-shaped coils are formed by wound multiple conductor layers and by inserting an insulator layer between neighboring conductor layers.

Specifically, the 8-figure coil 17b consists of two rectangular plane-shaped-coils of 1×15×20 mm, the leading edge of a FET probe is connected to each coil, the terminal portion of the FET probe is connected to a digital oscilloscope 25 of a 2 GHz band as a wave-form observation device. Further, the 8-figure shaped coil 17b is placed at a center portion in the rectangular multi-wound plane shaped coil 17a, and on a three-dimension precision stage for fine adjustment of an angle and a position of the 8-figure shaped coil 17b. In this case, the winding number of the rectangular multi-wound plane shaped coil 17a is 5 and the dimensions of it are 20×50×100 mm. As described above, the FET probe 21 is used for reducing an adverse effect from the signal-transfer line as low as possible when the rectangular multi-wound plane shaped coil 17b is connected to the wave-form observation device 25 through the signal transfer cable 23.

The wave-form observation device 25 inputs and stores the wave form of an induced voltage of the 8-figure shaped coil 17b. A computer 27 controls the high frequency signal generating device 11, the high frequency power source 13, and the wave form measuring device 25. For example, the computer 27 controls the operation of the oscilloscope, and inputs and outputs data from and to the other devices in order to perform data processing.

Further, the entire measuring device is placed and covered by an electromagnetic shielding material which is not shown in the diagram.

In addition, in the magnetic property measuring apparatus, in order to correct the signal transfer property between the detecting coil and the wave form measuring device 25, first the signal transfer property A is obtained, and then the data of it is stored in a memory of the computer 27 in order to carry out an appropriate calculation for correction.

The procedure of the calculation for correction is following:

$$V=V_0/A \quad (12)$$

where, V is a voltage of a coil, $V_0$ is a measured voltage of an oscilloscope.

Figure 18:
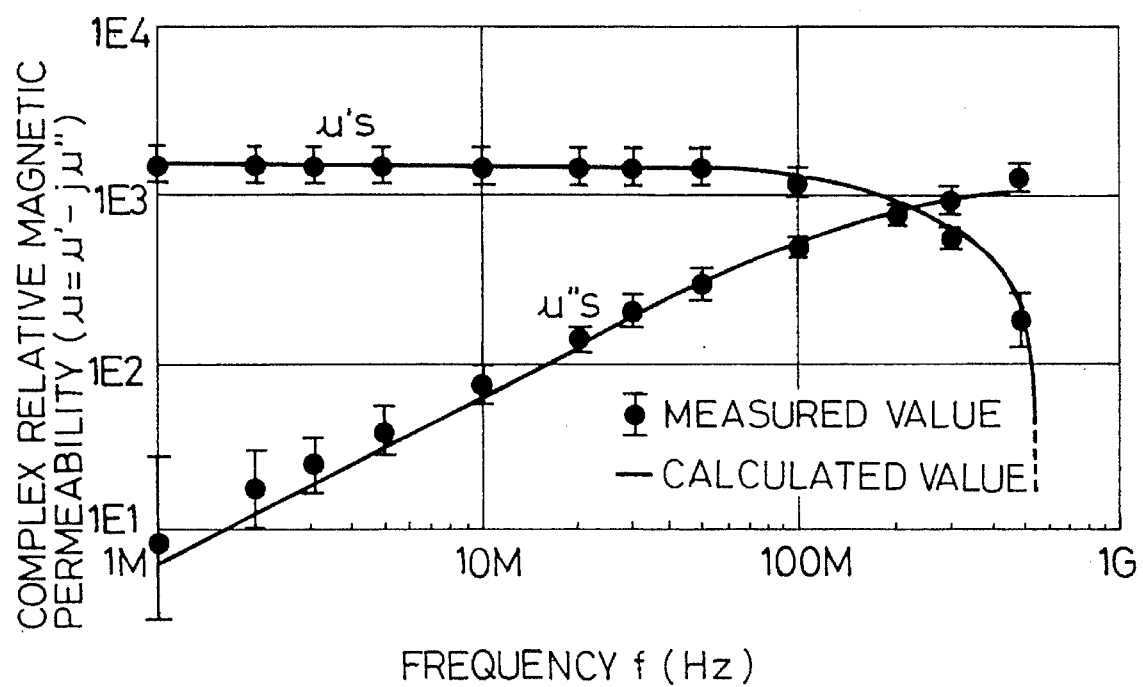
FIG. 18 is a graph showing an example of measured results of a complex relative magnetic permeability of the soft magnetic material by the high frequency magnetic property measuring apparatus shown in FIG. 17.

FIG. 18 is a graph showing a frequency property of a complex relative permeability on the magnetic hard axis of a soft magnetic thin film of an amorphous CoZrNb with uniaxial anisoropy of 2 μm thick measured by the magnetic property measuring apparatus.

This soft magnetic material sample is formed by a RF magnetron spattering method and is heat treated in a direct current magnetic field of 800 kA/m at 400° C.

An initial-permeability of the soft magnetic material sample obtained is estimated to be 1500, an anisotropy field is 480 A/m. In the soft magnetic material sample, stripe magnetic domains comprising only magnetic domains of 180° are observed.

The black colored points shown in FIG. 18 indicate that the measured values at the magnetic field amplitude is 1 A/m obtained by the apparatus of the invention. The solid lines designate calculated values obtained from the Landau-Lifshitz's equation and the effect of eddy current. In this case, the measured values are substantially equivalent to the calculated values.

Figure 19:
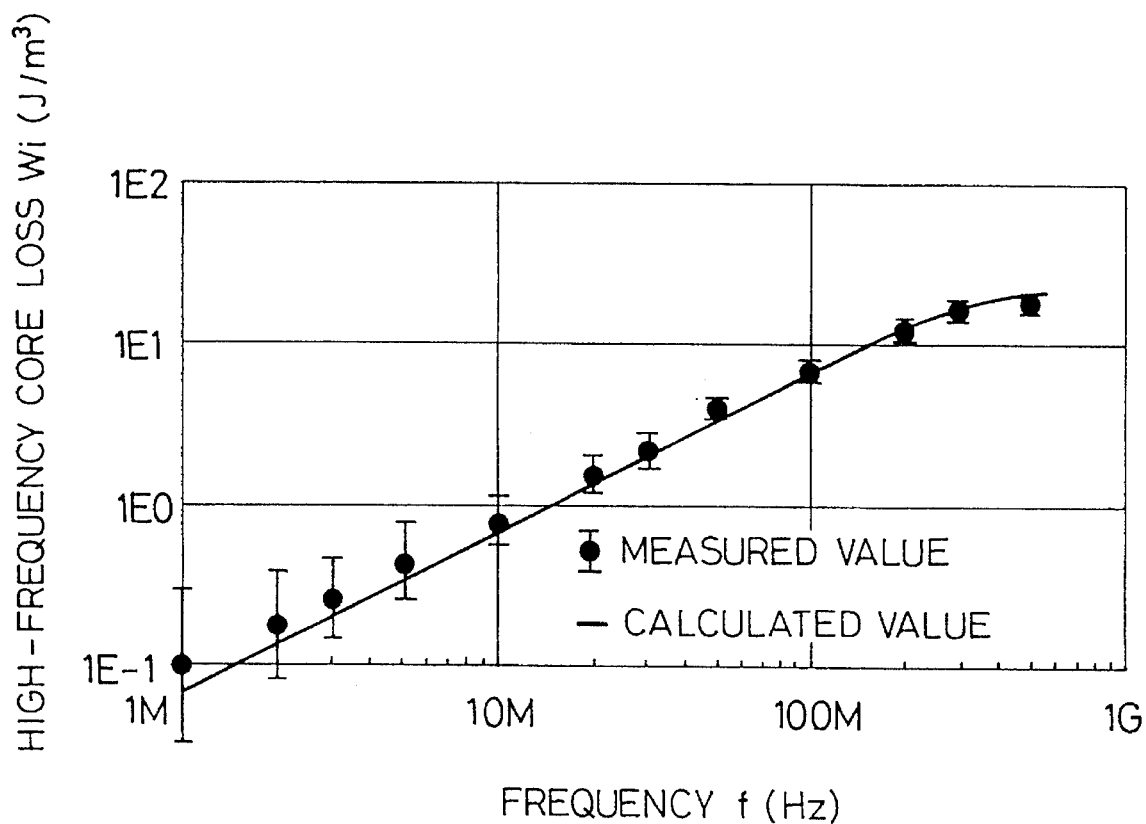
FIG. 19 is a graph showing an example of measured results of a high frequency core loss of the soft magnetic material by the high frequency magnetic property measuring apparatus shown in FIG. 17.

In addition, the core loss per unit volume, per one period is shown in FIG. 19 in which the value of a magnetization of a soft magnetic material sample is 0.1 T. In FIG. 19, the black colored points are measured values and the solid lines are calculated values obtained by the same calculation described above. In this case, the measured values are substantially, also, equivalent to the calculated values. The reason is that a soft magnetic material sample has a simple magnetic domain structure. In this case, the magnetic hard axis excitation can be explained by a rotational magnetization.

As described above in detail, the magnetic property measuring apparatus of the present invention can measure many kinds of cases, such as an initial-permeability with a small magnetic amplitude and a core loss with a large magnetic amplitude.

Specifically, the magnetic property measuring apparatus of the present invention can evaluate the high frequency magnetic properties of soft magnetic materials with a range of several MHz to several hundred MHz, in addition, the permeability of them can also be measured when the amplitude of the magnetic field is decreased. Further, a high frequency core loss can also be measured when the amplitude of the magnetic field is increased.

The magnetic amplitude over 80 A/m and the spatial fluctuation of the magnetic field can be decreased within less than 1% by the present invention. Moreover, the overall property of a soft magnetic material sample can also be measured.

Thus, it is helpful for material engineers to develop soft magnetic material. In addition, it can also provide the selection method to select an optimum soft magnetic material for engineers in the magnetic recording field and other system development fields.

What is claimed is:

1. A high frequency magnetic property measuring apparatus for soft magnetic film, comprising:

detection means for detecting the intensity of magnetization generated in a sample material to be measured, said detection means having a plane-shaped conductor having four edges comprising two pairs of opposite edges, opposite edges of one pair being in close proximity to each other to form a first internal cavity in which said material is placed;

magnetic field generation means for generating a homogeneous high frequency magnetic field using a plane-shaped conductor having four edges comprising two pairs of opposite edges, opposite edges of one pair being in close proximity to each other to form a second internal cavity in which said detection means is placed;

a power source for supplying a high frequency current to said magnetic field generation means; and data processing means for obtaining high frequency magnetic property measurements of said sample material using a detection signal output from said detection means.

2. A high frequency magnetic property measuring apparatus for soft magnetic film as claimed in claim 1, wherein said detection means is formed by a plane-shaped conductor pair having first and second conductors, the first and second conductors of said plane-shaped conductor pair electrically connected to each other in series to form an 8-figure-shaped form in cross section.

3. A high frequency magnetic property measuring apparatus for soft magnetic film as claimed in claim 1, wherein said detection means is formed by a plane-shaped conductor pair having a configuration in which a plane-shaped conductor is placed above another plane-shaped conductor by a predetermined space interval for electrically insulating the conductors from each other.

4. A high frequency magnetic property measuring apparatus for soft magnetic film as claimed in claim 1, wherein said data processing means comprises waveform memory means for storing data of the intensity of magnetization transferred from said detection means, wherein said data processing means stores in said waveform memory means first-type data provided from said detection means when said sample material is placed in said detection means, and said data processing means stores in said waveform memory means second-type data provided from said detection means when said sample material is not placed in said detection means and generates said high frequency magnetic property measurements based on a comparison of said first-type data and said second-type data stored in said waveform memory means.

5. A high frequency magnetic property measuring apparatus for soft magnetic film as claimed in claim 1, wherein a length of said magnetic field generation means is larger than a length of said detection means such that said detection means fits inside said second internal cavity.

6. A high frequency magnetic property measuring apparatus for soft magnetic film as claimed in claim 1, wherein the cross section of said detection means has a rectangular form.

7. A high frequency magnetic property measuring apparatus for soft magnetic film as claimed in claim 1, wherein the cross section of said magnetic field generation means has a rectangular form.

8. A high frequency magnetic property measuring apparatus for soft magnetic film as claimed in claim 1, wherein the detection means is placed at a center portion in said second internal cavity of said magnetic field generation means.

9. A magnetic field generation device for generating a homogeneous high frequency magnetic field, comprising:

a plane-shaped conductor having four edges comprising two pairs of opposite edges, opposite edges of one pair being in close proximity to each other to form an internal cavity, said plane-shaped conductor receiving a high frequency current provided from an external power source to thereby generate said homogeneous high frequency magnetic field.

10. A magnetic detection device for obtaining the intensity of a magnetization in a sample material to be measured, comprising:

a plane-shaped conductor having four edges comprising two pairs of opposite edges, opposite edges of one pair being in close proximity to each other to form an internal cavity, said conductor having electrical terminals; and a circuit to detect a voltage signal which occurs between said electrical terminals in proportion to the intensity of magnetization in said sample material placed in said internal cavity of said plane-shaped conductor when said magnetic detection device is placed in a homogeneous high frequency magnetic field.

* * * * *